United States Patent
Koh

(10) Patent No.: US 7,628,757 B1
(45) Date of Patent: Dec. 8, 2009

(54) SYSTEM AND METHOD FOR IMPEDANCE-BASED DETECTION OF PULMONARY EDEMA AND REDUCED RESPIRATION USING AN IMPLANTABLE MEDICAL SYSTEM

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 742 days.

(21) Appl. No.: 11/138,229

(22) Filed: May 25, 2005

(51) Int. Cl.
  *A61B 5/08* (2006.01)
(52) U.S. Cl. .................................................. 600/484
(58) Field of Classification Search .................. 600/484
  See application file for complete search history.

(56) References Cited

U.S. PATENT DOCUMENTS

| | | | |
|---|---|---|---|
| 3,593,718 A | 7/1971 | Krasner et al. | |
| 5,056,519 A | 10/1991 | Vince | 128/419 G |
| 5,328,460 A | 7/1994 | Lord et al. | 604/67 |
| 5,476,483 A | 12/1995 | Bornzin et al. | 607/17 |
| 5,876,353 A | 3/1999 | Riff | 600/547 |
| 5,911,218 A | 6/1999 | DiMarco | 128/200.24 |
| 5,957,861 A | 9/1999 | Combs et al. | 600/547 |
| 5,974,340 A | 10/1999 | Kadhiresan | 607/18 |
| 6,128,534 A | 10/2000 | Park et al. | 607/17 |
| 6,331,536 B1 | 12/2001 | Radulovacki et al. | 514/214.02 |
| 6,415,183 B1 | 7/2002 | Scheiner et al. | 607/42 |
| 6,432,956 B1 | 8/2002 | Dement et al. | 514/252.1 |
| 6,438,408 B1 | 8/2002 | Mulligan et al. | 600/510 |
| 6,449,509 B1 | 9/2002 | Park et al. | 607/20 |
| 6,473,640 B1 | 10/2002 | Erlebacher | 600/547 |
| 6,512,949 B1 | 1/2003 | Combs et al. | 600/547 |
| 6,512,952 B2 | 1/2003 | Stahmann et al. | 607/9 |
| 6,519,493 B1 | 2/2003 | Florio et al. | 607/9 |
| 6,525,073 B2 | 2/2003 | Mendel et al. | 514/337 |
| 6,572,557 B2 | 6/2003 | Tchou et al. | 600/483 |
| 6,586,478 B2 | 7/2003 | Ackman et al. | 514/738 |
| 6,595,927 B2 | 7/2003 | Pitts-Crick et al. | 600/529 |
| 6,622,045 B2 | 9/2003 | Snell et al. | 607/30 |
| 6,628,988 B2 | 9/2003 | Kramer et al. | 607/9 |
| 6,643,546 B2 | 11/2003 | Mathis et al. | 607/9 |

(Continued)

FOREIGN PATENT DOCUMENTS

WO   WO 2004/ 047638   6/2004

OTHER PUBLICATIONS

NonFinal Office Action, mailed Mar. 25, 2008: Related U.S. Appl. No. 11/138,219.

*Primary Examiner*—Charles A Marmor, II
*Assistant Examiner*—Christian Y Jang

(57) ABSTRACT

Techniques are provided for detecting pulmonary edema based on a comparison of impedance-based respiratory patterns and impedance-based cardiac patterns, i.e. patterns derived from thoracic impedance signals. In one example, a numerical ratio is calculated between average peak-to-peak amplitudes of the respiratory patterns and average peak-to-peak amplitudes of the cardiac patterns. Pulmonary edema is detected if the amplitude ratio falls below a pulmonary edema detection threshold. Techniques are also provided for controlling operation of an impedance-based reduced respiration detector, i.e. a detector which seeks to detect apnea, hypopnea, or the like, based on analysis of respiratory patterns derived from a thoracic impedance signal. If the numerical ratio falls below a minimum reliability threshold, then the reduced respiration detector is deactivated because episodes of reduced respiration cannot then reliably be derived from an analysis of respiration patterns obtained from the thoracic impedance signals.

5 Claims, 11 Drawing Sheets

U.S. PATENT DOCUMENTS

| | | |
|---|---|---|
| 6,645,153 B2 | 11/2003 | Kroll et al. .................. 600/481 |
| 6,829,503 B2 | 12/2004 | Alt ............................. 600/547 |
| 6,931,272 B2 * | 8/2005 | Burnes ....................... 600/509 |
| 2002/0032383 A1 | 3/2002 | Weil et al. |
| 2002/0161310 A1 | 10/2002 | Daum |
| 2003/0216789 A1 | 11/2003 | Deem et al. .................... 607/9 |
| 2004/0102712 A1 | 5/2004 | Belalcazar et al. .......... 600/547 |
| 2006/0041280 A1 | 2/2006 | Stahmann et al. |
| 2006/0135877 A1 * | 6/2006 | Giftakis et al. .............. 600/513 |
| 2006/0241512 A1 * | 10/2006 | Kwok et al. ................. 600/547 |
| 2006/0258952 A1 | 11/2006 | Stahmann et al. |
| 2006/0264776 A1 | 11/2006 | Stahmann et al. |
| 2006/0293609 A1 | 12/2006 | Stahmann et al. |

* cited by examiner

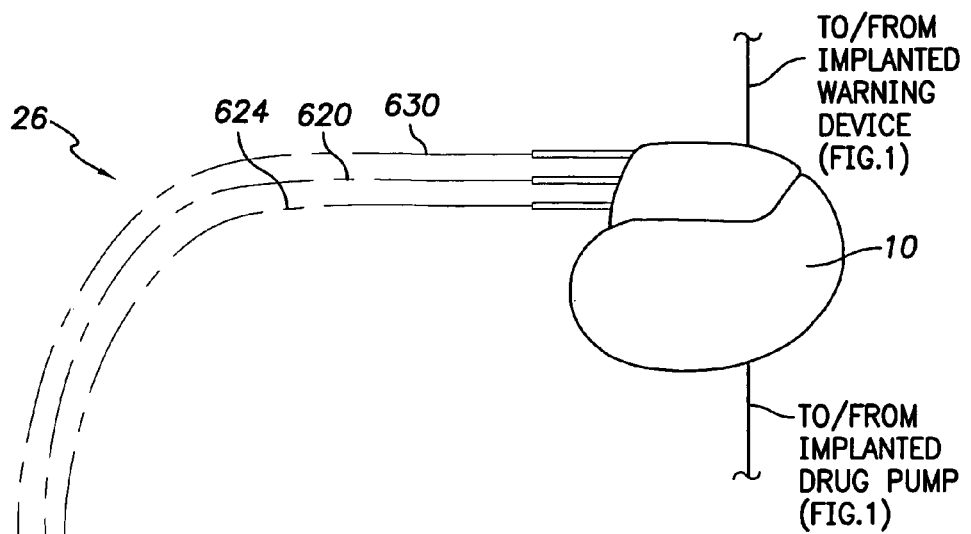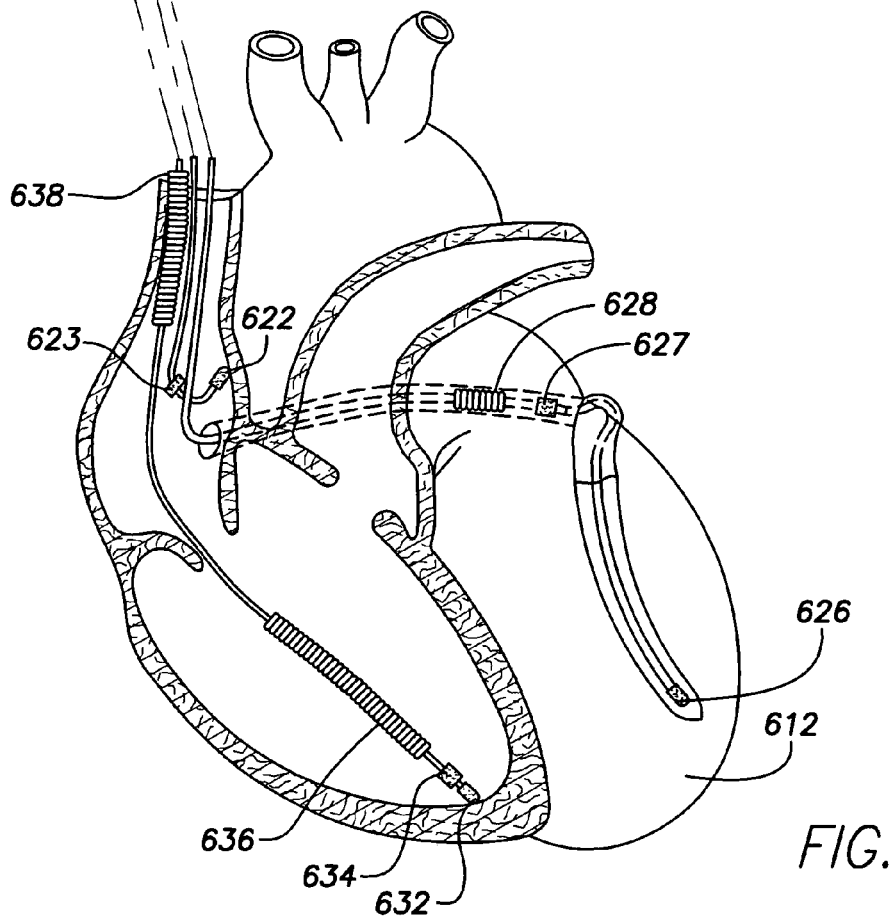
FIG. 11

SYSTEM AND METHOD FOR IMPEDANCE-BASED DETECTION OF PULMONARY EDEMA AND REDUCED RESPIRATION USING AN IMPLANTABLE MEDICAL SYSTEM

FIELD OF THE INVENTION

This application is related to copending U.S. patent application Ser. No. 11/138,219, filed May 25, 2005, entitled "System and Method for Impedance-Based Detection of Pulmonary Edema and Reduced Respiration Using an Implantable Medical System".

FIELD OF THE INVENTION

The invention generally relates to implantable medical devices, such as pacemakers or implantable cardioverter/defibrillators (ICDs), and in particular to impedance-based techniques for detecting pulmonary edema arising due to heart failure, and also to techniques for detecting apnea, within a patient in which a medical device is implanted and for delivering therapy in response thereto.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing."

Pulmonary edema is a swelling and/or fluid accumulation in the lungs often caused by heart failure (i.e. the edema represents one of the "congestives" of CHF.) Briefly, the poor cardiac function resulting from heart failure can cause blood to back up in the lungs, thereby increasing blood pressure in the lungs. The increased pressure pushes fluid—but not blood cells—out of the blood vessels and into lung tissue and air sacs. This can cause severe respiratory problems and, left untreated, can be fatal. Pulmonary edema is usually associated with relatively severe forms of heart failure and is often asymptomatic until the edema itself becomes severe, i.e. the patient is unaware of the pulmonary edema until it has progressed to a near fatal state when respiration suddenly becomes quite difficult.

In view of the potential severity of heart failure/pulmonary edema, it is highly desirable to detect the onset of these conditions within a patient and to track the progression thereof so that appropriate therapy can be provided. Many patients suffering heart failure/pulmonary edema already have pacemakers or ICDs implanted therein or are candidates for such devices. Accordingly, it is desirable to provide such devices with the capability to automatically detect and track heart failure/pulmonary edema.

Heretofore, a number of techniques have been developed for detecting heart failure and/or pulmonary edema using implantable cardiac devices based on analysis of a thoracic impedance signal. See, for example, U.S. Pat. No. 5,876,353 to Riff, entitled "Impedance Monitor for Discerning Edema through Evaluation of Respiratory Rate"; U.S. Pat. No. 5,957,861 to Combs et al., entitled "Impedance Monitor for Discerning Edema through Evaluation of Respiratory Rate"; U.S. Pat. No. 6,512,949 also to Combs et al., entitled "Implantable Medical Device for Measuring Time Varying Physiologic Conditions Especially Edema and for Responding Thereto"; U.S. Pat. No. 6,473,640 to Erlebacher, entitled "Implantable Medical Device for Measuring Time Varying Physiologic Conditions Especially Edema and for Responding Thereto"; U.S. Pat. No. 6,595,927 to Pitts-Crick et al., entitled "Method and System for Diagnosing and Administering Therapy of Pulmonary Congestion"; U.S. Pat. No. 6,829,503 to Aft, entitled "Congestive Heart Failure Monitor"; and U.S. Patent Application 2004/0102712 of Belalcazar et al., entitled "Impedance Monitoring for Detecting Pulmonary Edema and Thoracic Congestion."

However, it would be desirable to provide improved techniques, particularly for detecting pulmonary edema, via thoracic impedance and is to this end that aspects of the invention are directed. In this regard, previous techniques for detecting pulmonary edema based on impedance are often unduly complex. In some cases, changes in impedance due to other factors besides the fluids associated with pulmonary edema can possibly result in a false positive detection of pulmonary edema.

Many patients with heart failure and/or pulmonary edema also suffer from episodes of reduced respiration, such as apnea or hypopnea. With hypopnea, respiration is reduced but is still present. With apnea, however, respiration may cease completely for a minute or longer. One common form of apnea is sleep apnea, in which episodes can occur hundreds of times during a single night. Accordingly, patients with sleep apnea experience periodic wakefulness at night and excessive sleepiness during the day. In addition, apnea can exacerbate various medical conditions, particularly CHF.

One form of apnea is central sleep apnea (CSA), which is believed to be the result of a neurological condition. Briefly, respiration is regulated by groups of nerve cells in the brain in response to changing blood chemistry levels, particularly blood $CO_2$ levels. When blood $CO_2$ levels exceed a certain threshold, the groups of nerve cells generate a burst of nerve signals for triggering inspiration. The inspiration nerve signals are relayed via phrenic nerves to the diaphragm and via other nerves to chest wall muscles, which collectively contract to expand the lungs. With CSA, the nerve signals are not properly generated during extended periods of time while the patient is asleep or are of insufficient magnitude to trigger sufficient muscle contraction to achieve inhalation. In either case, the patient thereby fails to inhale until appropriate inspiration nerve signals are eventually generated—often not until after the patient awakes in response to significantly high blood $CO_2$ levels. Arousal from sleep due to CSA usually lasts only a few seconds, but such brief arousals nevertheless disrupt continuous sleep and can prevent the patient from achieving rapid eye movement (REM) sleep, which is needed. In addition, as already noted, frequent periods of apnea can exacerbate other medical conditions. In particular, aberrant blood chemistry levels occurring by sleep apnea are a significant problem for patients with CHF. Due to poor cardiac function caused by CHF, patients already suffer from generally low blood oxygen levels. Frequent periods of sleep apnea result in even lower blood oxygen levels. Fortunately, CSA is rare.

Another form of apnea, which is more common, is obstructive sleep apnea (OSA) wherein the respiration airway is temporarily blocked. With OSA, proper inspiration nerve signals are generated by the brain and so the diaphragm and chest muscles contract in an attempt to cause the lungs to inhale. However, an obstruction of the respiration airway blocks delivery of air to the lungs and so blood $CO_2$ levels continue to increase, usually until the patient awakens and readjusts his or her position so as to reopen the obstructed respiration pathway so that normal breathing can resume. The site of obstruction is usually the soft palate, near the base of the tongue, which lacks rigid structures such as bone or cartilage for keeping the airway open. While the patient is awake, muscles near the soft palate keep the passage open. However, while asleep, the muscles can relax to a point where the airway collapses and hence becomes obstructed. As with CSA, arousal from sleep usually lasts only a few seconds but is sufficient to disrupt continuous sleep and prevent proper REM sleep. It is estimated that OSA occurs in approximately two percent of women and four percent of men over the age of thirty-five. Obesity is a significant contributing factor. In addition, patients are at greater risk of OSA with increasing age, due to loss of muscle mass, particularly within the muscles that would otherwise hold the respiration airway open.

Apnea can also occur during Cheyne-Stokes Respiration (CSR), which is an abnormal respiratory pattern often occurring in patients with CHF. CSR is characterized by alternating periods of hypopnea and hyperpnea (i.e. fast, deep breathing.) Briefly, CSR arises principally due to a time lag between blood $CO_2$ levels sensed by the respiratory control nerve centers of the brain and the blood $CO_2$ levels. With CHF, poor cardiac function results in poor blood flow to the brain such that respiratory control nerve centers respond to blood $CO_2$ levels that are no longer properly representative of the overall blood $CO_2$ levels in the body. Hence, the respiratory control nerve centers trigger an increase in the depth and frequency of breathing in an attempt to compensate for perceived high blood $CO_2$ levels—although the blood $CO_2$ levels have already dropped. By the time the respiratory control nerve centers detect the drop in blood $CO_2$ levels and act to slow respiration, the blood $CO_2$ levels have already increased. This cycle becomes increasingly unbalanced until respiration alternates between hypopnea and hyperpnea. The periods of hypopnea often become sufficiently severe that no breathing occurs between the periods of hyperpnea, i.e. periods of frank apnea occur between the periods of hyperpnea. The wildly fluctuating blood chemistry levels caused by alternating between hyperpnea and apnea/hypopnea can significantly exacerbate CHF and other medical conditions. When CHF is still mild, CSR usually occurs, if at all, only while the patient is sleeping. When it becomes more severe, CSR can occur while the patient is awake. Accordingly, CSR is one mechanism by which apnea can occur within patients who are awake. Apnea can also occur while awake due to neurological disorders or other factors. Hence, apnea is not limited to occurring only within sleeping patients.

Note that, in some of the literature, apnea arising due to CSR caused by CHF is categorized as a type of CSA (i.e. central sleep apnea), even though the apnea is not the result of a disorder of the central nervous system and even though it does necessarily occur only while the patient is asleep. Herein, however, CSA is only used to refer to apnea arising from a disorder of the central nervous system that occurs while a patient is asleep, as described above. Apnea/hypopnea arising because of CHF (such as via the mechanism of CSR respiration) is instead referred to herein as "CHF-induced apnea/hypopnea."

In view of the significant adverse consequences of apnea/hypopnea, particularly insofar as patients with CHF are concerned, it is highly desirable to provide techniques for detecting individual episodes of the condition. A variety of techniques have been developed thus far. In particular, techniques have been developed that track changes in thoracic impedance as a means for tracking respiration so as to permit detection of apnea/hypopnea. In other words, the same impedance signal analyzed to detect heart failure/pulmonary edema can also be used to detect apnea. See, e.g., U.S. patent application Ser. No. 10/883,857, filed Jun. 30, 2004, entitled "System And Method For Real-Time Apnea/Hypopnea Detection Using An Implantable Medical System (A04P1057); U.S. patent application Ser. No. 10/844,023, filed May 11, 2004, entitled "System and Method for Providing Demand-Based Cheyne-Stokes Respiration Therapy Using an Implantable Medical Device" (A04P1042); and U.S. Pat. No. 6,449,509 to Park et al., entitled "Implantable Stimulation Device having Synchronous Sampling for a Respiration Sensor." See, also, U.S. Pat. No. 5,974,340 to Kadhiresan, entitled "Apparatus and Method for Monitoring Respiratory Function in Heart Failure Patients to Determine Efficacy of Therapy."

Problems, however, can arise when attempting to detect apnea/hypopnea via thoracic impedance in patients with pulmonary edema. The present inventor has noted that apnea detection via thoracic impedance is most reliable when the lungs are clear but is considerably less reliable when the lungs are filled with fluids, i.e. when the patient suffers from pulmonary edema. Hence, it is not always possible to reliably detect apnea using an impedance-based detection technique if the patient suffers from pulmonary edema. Accordingly, in addition to providing improved impedance-based techniques for detecting pulmonary edema as noted above, it is also desirable to provide techniques for determining when impedance-based reduced respiration detection techniques can reliably be used. It is to this end that other aspects of the invention are directed.

SUMMARY

In accordance with a first illustrative embodiment, techniques are provided for detecting pulmonary edema within a patient using an implantable medical device. Briefly, a comparison value representative of a comparison of impedance-based respiratory patterns and impedance-based cardiac patterns is determined. Then, pulmonary edema is detected based on the comparison value.

In an example, the comparison value is representative of a numerical ratio of average peak-to-peak amplitudes of impedance-based respiratory patterns and average peak-to-peak amplitudes of the impedance-based cardiac patterns. More specifically, time-varying impedance, signals are low pass filtered to derive respiratory patterns, i.e. cyclical patterns representative of thoracic movement due to respiration. The same signals are also high pass filtered to derive cardiac patterns, i.e. cyclical patterns representative of the beating of the heart of the patient. An average peak-to-peak amplitude of the respiration pattern is calculated (i.e. a value representative of the difference between the positive peaks and the opposing negative peaks within the respiration pattern) over a period of one minute while the patient is asleep. Average peak-to-peak amplitudes of the cardiac pattern are also calculated based on data collected over the same one-minute period. Then, the numerical ratio of the two average amplitude values is determined for use in detecting pulmonary edema. To this end, this amplitude ratio value is compared against a pulmonary edema threshold value. So long as the amplitude ratio remains above the threshold, the lungs are reasonably free of fluids. However, if the amplitude ratio falls below the threshold, this is an indication that pulmonary edema has occurred within the patient and the lungs are filled with fluids.

The amplitude ratio is lower during pulmonary edema because the fluids within the lungs associated with pulmonary edema reduce the amount of variation within the impedance signals due to respiration. A reduction in the ratio occurs even if actual respiration effort remains the same. In other words, the decrease in the peak-to-peak amplitudes of the impedance-based respiration patterns relative to the peak-to-peak amplitudes of the impedance-based cardiac patterns occurs due to the presence of the fluids in the lung and not merely due to any decrease in respiratory effort. Indeed, during pulmonary edema, respiratory effort often increases as the patient attempts to breathe more deeply to compensate for the reduction in oxygen entering the blood stream due to the fluidic lung.

By detecting pulmonary edema based on a comparison of impedance-based respiratory patterns and impedance-based cardiac patterns, a simple detection technique is thereby provided. Moreover, because detection is based on a comparison of respiratory patterns and cardiac patterns, changes in the impedance of the respiratory patterns due to factors besides lung fluid levels are not likely to lead to erroneous detection of pulmonary edema. In this regard, the presence of lung fluids does not significantly affect the amplitude of the cardiac component of the impedance signals. Hence, the cardiac components provide a convenient baseline against which changes in the impedance of the respiratory patterns due to lung fluid can reliably be detected. In contrast, if only impedance-based respiratory patterns are analyzed, changes in the amplitudes of the patterns cannot necessarily be related to changes in lung fluid levels, as such changes could be due to other factors.

In many cases, pulmonary edema is associated with heart failure. Otherwise conventional techniques can be used to determine whether pulmonary edema detected via the comparison technique of the invention is due to heart failure or is instead due to some other condition.

In accordance with a second aspect of the invention, techniques are provided for controlling an impedance-based reduced respiration detector within a patient using an implantable medical device. Briefly, a value representative of a comparison of impedance-based respiratory patterns and impedance-based cardiac patterns is determined. Then, the impedance-based reduced respiration detector is selectively activated based on the value.

In an example, the comparison value is again representative of the numerical ratio of average peak-to-peak amplitudes of impedance-based respiratory patterns and average peak-to-peak amplitudes of the impedance-based cardiac patterns. The amplitude ratio is compared against a respiration detector minimum reliability threshold value. So long as the ratio remains above the threshold, the reduced respiration detector can reliably be used to detect episodes of reduced respiration, i.e. apnea/hypopnea. However, if the ratio falls below the threshold, this is an indication that impedance-based techniques for detecting episodes of reduced respiration can no longer reliably be performed because variations in the impedance signals due to respiration are too severely diminished relative to those due to the beating of the heart. In other words, respiration patterns can no longer be reliably derived by low pass filtering impedance signals and hence a detector that seeks to detect episodes of reduced respiration based on an analysis of impedance signals can no longer be deemed reliable. If so, then an alternative technique for detecting episodes of reduced respiration detector is preferably employed. For example, an external sensor may be employed, such as a nasal thermistor or chest band sensor. Alternatively, implantable device-based detection techniques can be activated that do not rely on an analysis of impedance signals, such as blood pressure-based techniques.

Thus, techniques are set forth for detecting pulmonary edema and for controlling activation of an impedance-based reduced respiration detector within a patient. Preferably, both techniques are implemented. In one example, data representative of the impedance-based respiration amplitude/cardiac amplitude ratio is periodically stored for trend analysis. Separate thresholds are provided for detecting pulmonary edema and for deactivating an impedance-based reduced respiration detector. If the amplitude ratio falls below a first, higher threshold, pulmonary edema is thereby detected and appropriate warnings and therapies are automatically delivered. Given that pulmonary edema can be fatal, the warnings preferably mandate prompt medical attention. Any therapy that is automatically delivered by the implantable system preferably depends on the source of the pulmonary edema. For example, if pulmonary edema is due to congestive heart failure, CRT therapy may be activated in an attempt to improve cardiac output to decrease fluid retention in the lung. If an implantable drug pump is provided, any medications appropriate to pulmonary edema may automatically be delivered. Meanwhile, if the amplitude ratio falls below a second, lower threshold, then the impedance-based reduced respiration detector is deactivated and an alternate technique is employed. Diagnostic information representative of the trend of the amplitude ratio and representative of any therapies automatically delivered is preferably recorded within a memory of the implanted system for subsequent review by a physician.

BRIEF DESCRIPTION OF THE DRAWINGS

The above and further features, advantages and benefits of the invention will be apparent upon consideration of the descriptions herein taken in conjunction with the accompanying drawings, in which:

FIG. 11 is a simplified, partly cutaway view, illustrating the pacer/ICD of FIG. 1 along with a complete set of leads implanted in the heart of a patient.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
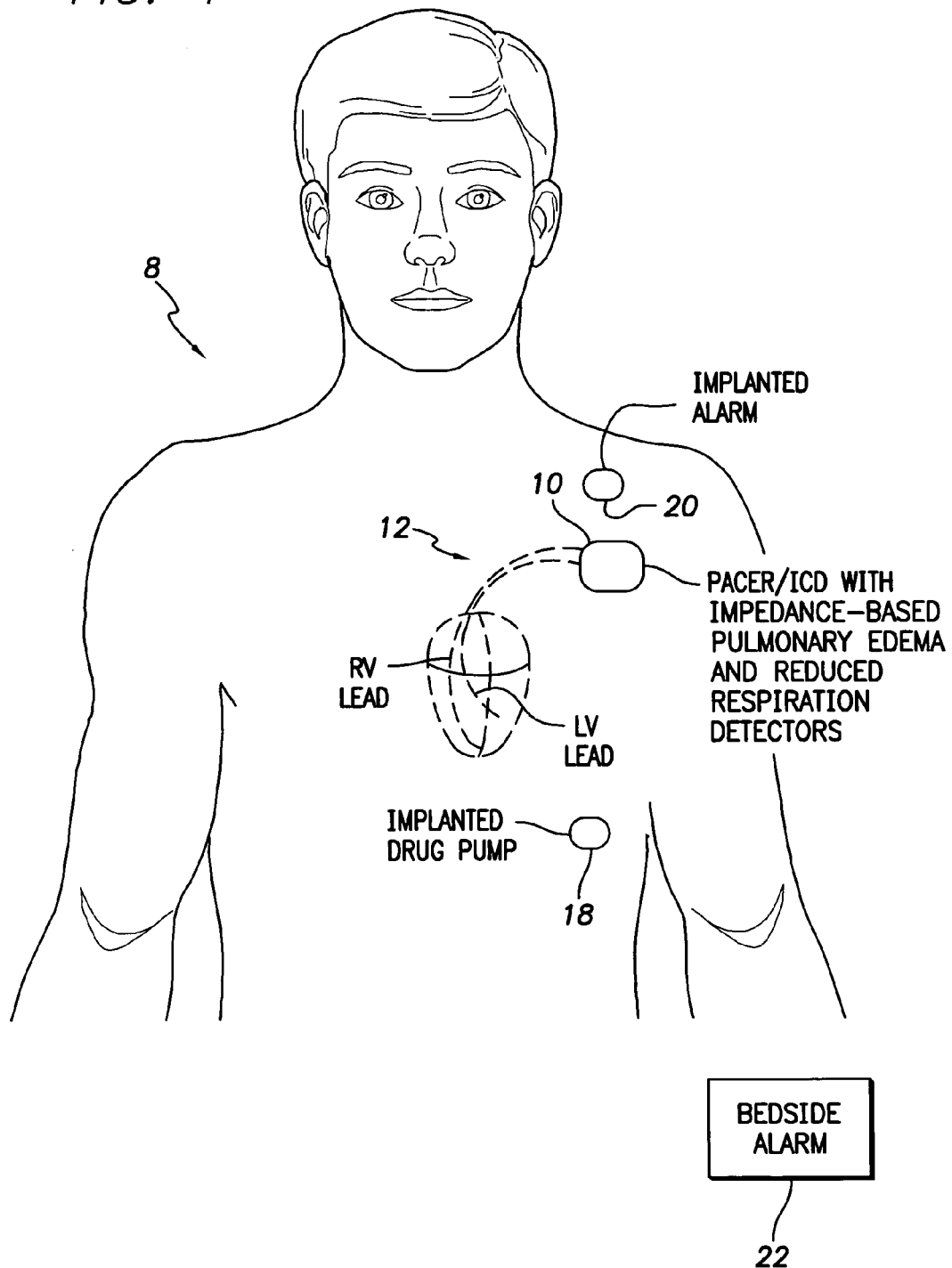
FIG. 1 illustrates pertinent components of an implantable medical system having a pacer/ICD equipped with impedance-based pulmonary edema and reduced respiration detectors.

FIG. 1 illustrates an implantable medical system 8 capable of detecting pulmonary edema and/or individual episodes of reduced respiration (i.e. apnea/hypopnea) via impedance analysis and delivering appropriate therapy and warnings. To this end, a pacer/ICD 10 (or other implantable medical device) receives impedance signals between an electrode mounted to a cardiac pacing lead 12 (only two of which are shown in FIG. 1) and an electrode mounted to the housing of the device. A complete set of exemplary pacing leads are shown in FIG. 11. The housing of the device is described with reference to FIG. 12. Techniques for detecting impedance are well known. See, for example, techniques set forth in the above-listed patents to Combs et al., Erlebacher, and Pitts-Crick et al. Based on the impedance signals, the pacer/ICD detects episodes of pulmonary edema using a comparison technique, summarized below with reference to FIGS. 2-6. The pacer/ICD also selectively activates an impedance-based reduced respiration detector using a related comparison technique, summarized below with reference to FIG. 7. Although a pacer/ICD is illustrated in FIG. 1, it should be understood that the techniques of the invention may be implemented within other implantable devices, particularly including dedicated detection devices not capable of cardiac stimulation therapy.

If pulmonary edema is detected, the system determines whether the edema is due to heart failure and delivers appropriate warnings and therapy. Warnings may be internally delivered to the patient via an implanted alarm 18 or may be transmitted to an external (i.e. bedside) monitor 20. Internal alarm 18 may be a vibrating device or a "tickle" voltage device that, in either case, provides perceptible stimulation to the patient to alert the patient or medical personnel to the onset of pulmonary edema. If an activity sensor is provided within the pacer/ICD, the form of the alarm may be controlled based on patient activity. For example, if the activity level indicates that the patient is asleep, a more noticeable alarm may be employed than if the patient is deemed to be awake. In addition, while the patient is asleep, the intensity of the alarm signal can be periodically increased until the patient awakens, as detected by the activity sensor. Drug therapy appropriate for pulmonary edema and/or heart failure may be delivered via an implantable drug pump 18. Discussions of possible medications for addressing pulmonary edema and/or heart failure are provided below.

If the reduced respiration detector is activated and if an episode of reduced respiration is then detected, the system identifies the type of reduced respiration (i.e. CSA, OSA, CHF-induced apnea/hypopnea) and deliver appropriates therapy. To this end, upper airway stimulators (not specifically shown) may be implanted near the soft palate region of the throat surrounding respiratory airway for stimulating adjacent muscles to increase muscle tone and expand the airway, thus alleviating airway blockage associated with OSA. Phrenic nerve stimulators (also not shown) may be implanted adjacent the phrenic nerves of the patient to rhythmically stimulate the diaphragm to cause the diaphragm to contract in response to CSA or CHF-induced/hypopnea. Upper airway stimulators and phrenic nerve stimulators are not shown in FIG. 1 as these components may be otherwise conventional and the invention is primarily directed to impedance-based detection techniques rather than to specific therapies. Also, in many implementations, such components are not provided.

If nerve stimulators for use in response to episodes of reduced respiration are not provided then, upon detection of an episode of reduced respiration, the pacer/ICD instead activates the internal alarm 20 or the external bedside alarm 22. Internal alarm 18 provides perceptible stimulation to the patient to alert or awaken the patient so as to terminate the episode of reduced respiration. The bedside alarm may provide audible or visual alarm signals of sufficient magnitude to alert or awaken the patient. Additionally, or in the alternative, the drug pump 18 may be equipped to deliver drug therapy in an attempt to prevent the onset of additional episodes of reduced respiration. Discussions of possible medications for use in response to reduced respiration are provided below.

In addition, the pacer/ICD may be controlled to deliver overdrive pacing for the purposes of preventing additional episodes of reduced respiration from occurring. In one example, upon the detection of initial episodes of reduced respiration, overdrive pacing and/or drug therapy is delivered to the patient in an attempt to prevent the onset of additional episodes of reduced respiration. If additional episodes nevertheless occur and the system is not equipped with stimulators for directly terminating the episode, then alarm signals are generated to alert or awaken the patient. Implantable upper airway muscle stimulators and phrenic nerve stimulators are preferable within patients suffering from chronic episodes of reduced respiration to allow individual episodes to be terminated without needing to repeatedly alert or awaken the patient.

Thus, FIG. 1 provides an overview of an implantable system for detecting pulmonary edema, for controlling operation of a reduced respiration detector, and for delivering warnings and therapy. The system is also preferably capable of detecting a wide range of arrhythmias and for delivering a wide range of other forms of therapy, which is described more fully below with reference to FIGS. 11-12. Internal signal transmission lines for interconnecting the various implanted components of FIG. 1 are not shown. Alternatively, wireless signal transmission may be employed. In addition, it should be appreciated that systems provided in accordance with invention need not include all the components shown in FIG. 1. In many cases, for example, the system will include only the pacer/ICD and its leads. All therapy will be in the form of cardiac stimulation therapy. Other implementations will employ internal or external alarms and drug pumps but no muscle and phrenic nerve stimulators. Also, note that the particular locations of the implanted components are merely exemplary. These are just a few exemplary embodiments. No attempt is made herein to describe all possible combinations of components that may be provided in accordance with the general principles of the invention.

Overview of Comparison Technique for Detecting Pulmonary Edema

Figure 2:
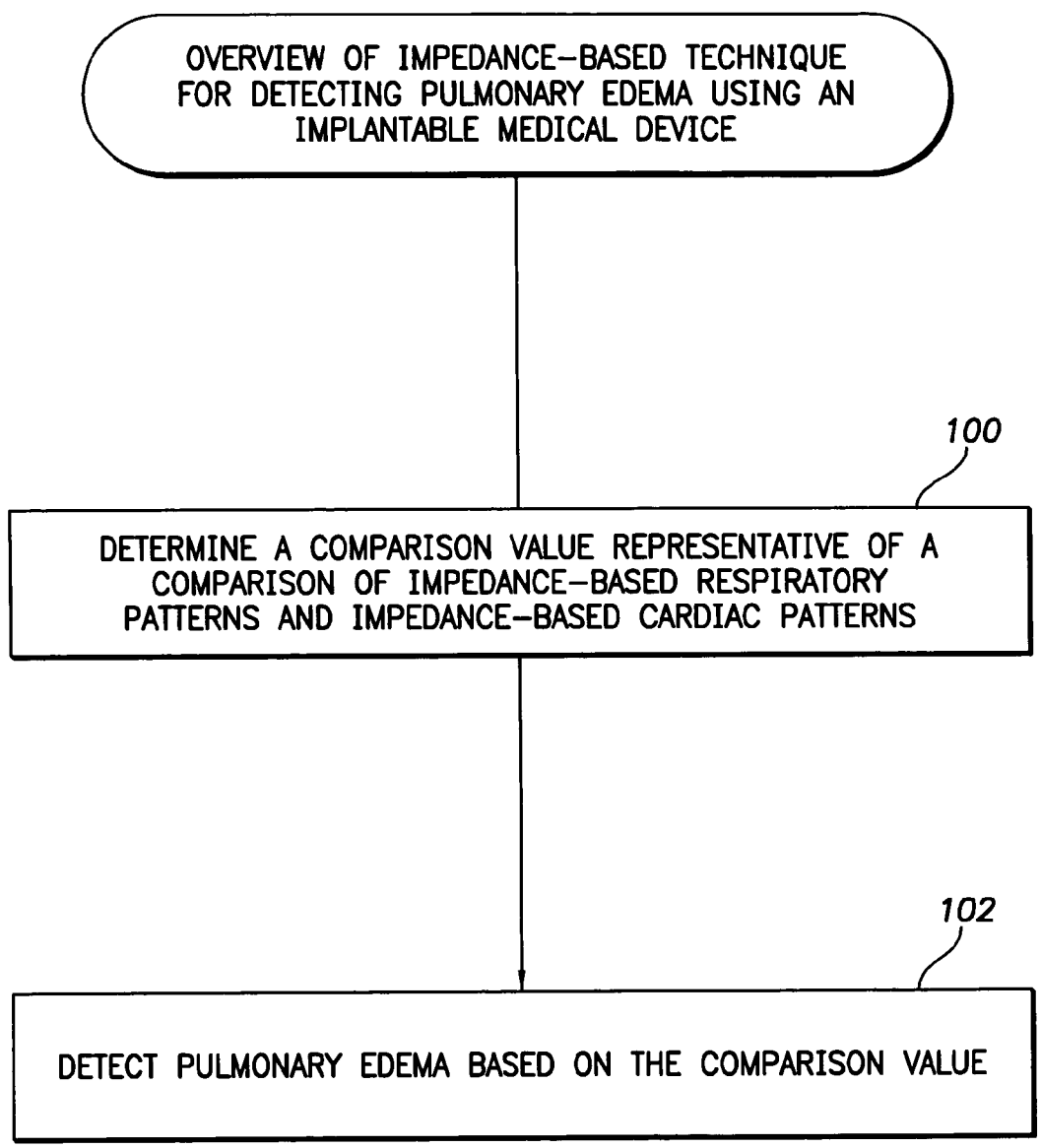
FIG. 2 is a flow diagram providing an overview of a method for detecting pulmonary edema performed by the impedance-based pulmonary edema detector of the system of FIG. 1.
Figure 3:
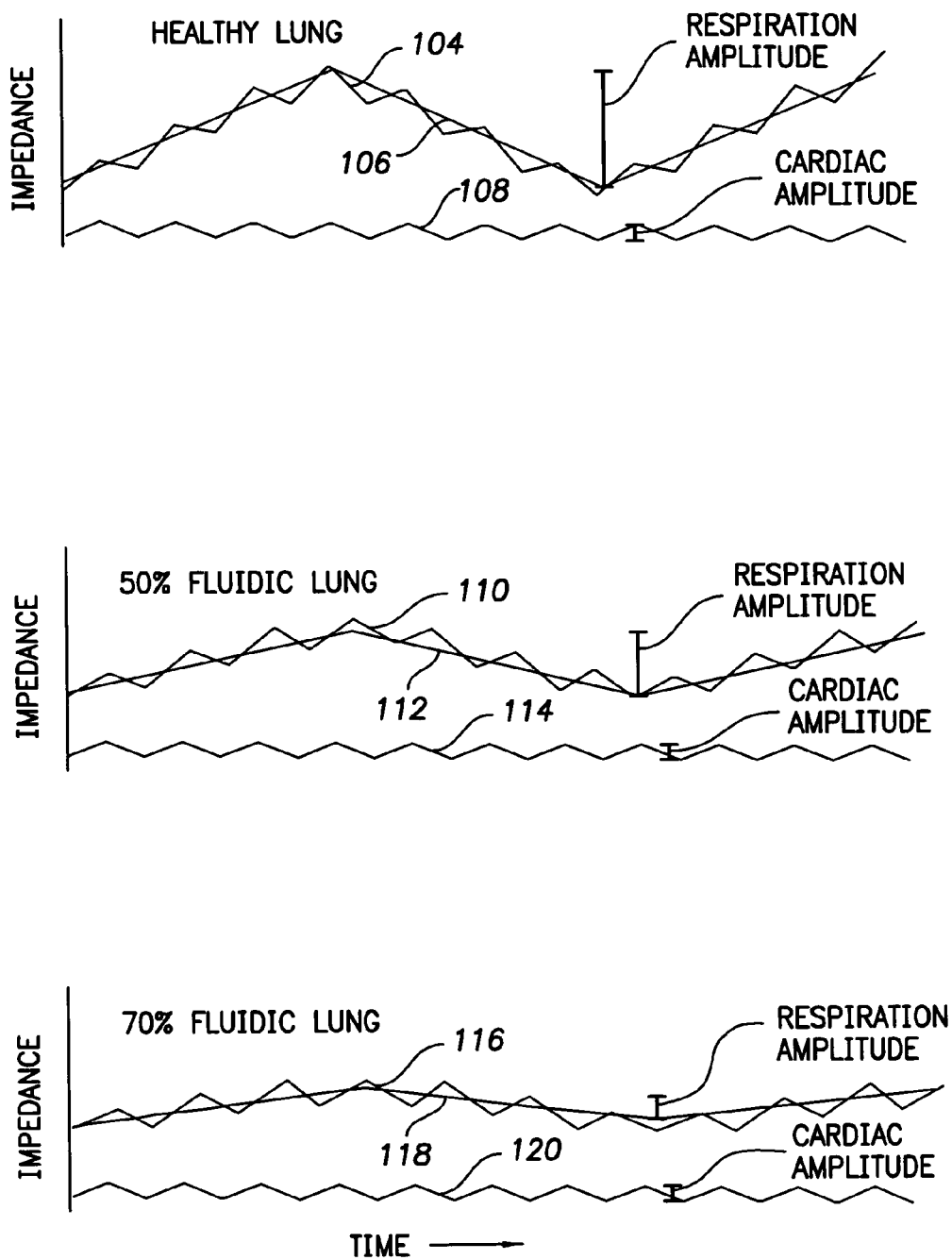
FIG. 3 provides exemplary, stylized graphs of impedance patterns for various lung fluid levels, which may be analyzed via the method of FIG. 2 to detect pulmonary edema.

FIG. 2 provides an overview of the techniques of the invention for use in detecting pulmonary edema using an implantable medical device. Briefly, at step 100, an implantable medical device (such as pacer/ICD of the FIG. 1) determines a value representative of a comparison of impedance-based respiratory patterns and impedance-based cardiac patterns. Then, at step 102, pulmonary edema is detected based upon the comparison value. This general procedure is illustrated by way of the exemplary graphs are set forth in FIGS. 3-6. Referring first to FIG. 3, a set of a stylized respiratory patterns and cardiac patterns are illustrated, along with a stylized representation of raw impedance signals from which they are derived. The vertical axis represents impedance (shown on arbitrary scale); whereas the horizontal axis represents time. Pattern 104 represents an impedance signal sensed in the heart of the patient having a generally healthy lung, i.e. a lung not filled with any substantial amounts of fluid. As can be seen, the impedance signal is modulated by a slowly varying respiratory component (separately illustrated by dotted line 106) as well as a more quickly varying cardiac component (separately illustrated by dotted line 108). In the examples of FIG. 3, there are about seven heartbeats per respiration cycle. This is merely exemplary. The respiratory component is due to expansion and contraction of the thorax during respiration. The cardiac component is due to the beating of the heart. As can be seen, for a healthy lung, the peak-to-peak respiration amplitude is significantly greater than the peak-to-peak cardiac amplitude. However, for a 50% fluidic lung, the peak-to-peak respiration amplitude is considerably lower than for the healthy lung. This is illustrated by way of impedance pattern 110, its respiratory component 112 and its cardiac component 114. For a 70% fluidic lung, the peak-to-peak respiration amplitude is even lower, as illustrated by impedance pattern 116, its respiratory component 118, and its cardiac component 120. Indeed, the peak-to-peak respiration amplitude for the 70% fluidic lung is about the same as the peak-to-peak amplitude of the cardiac pattern.

Thus, FIG. 3 illustrates that, whereas lung fluid does not significantly affect the cardiac component of the impedance signal, lung fluid does significantly affect the respiratory component of the impedance signal. Hence, a comparison of an impedance-based respiratory pattern and an impedance-based cardiac pattern provides information sufficient to detect the presence of fluids in the lung, i.e. to detect pulmonary edema, as summarized in FIG. 2.

Figure 4:
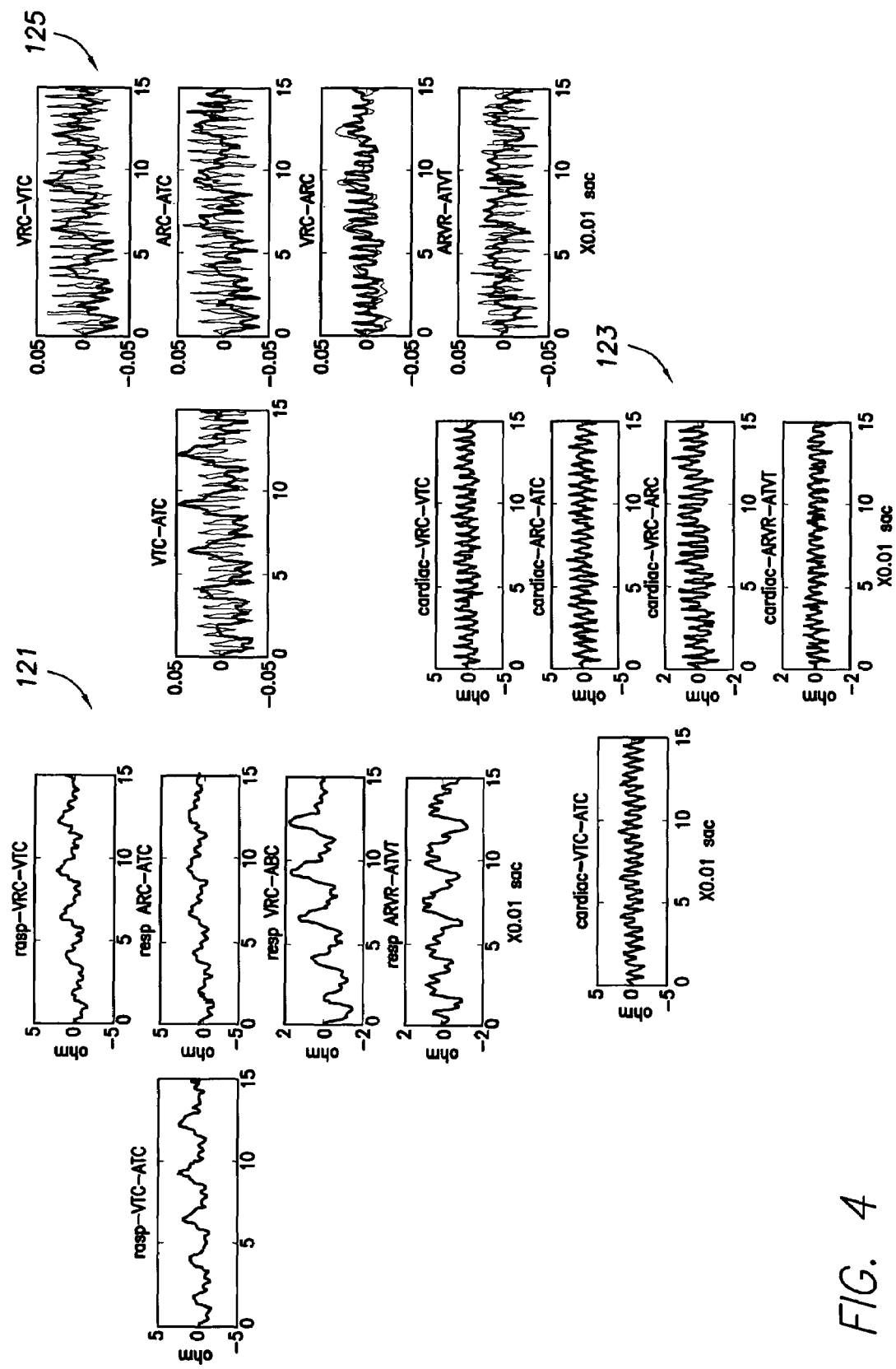
FIG. 4 provides actual impedance patterns analyzed for one particular lung fluid level.

Note that, to obtain the separate amplitudes of the cardiac components and the respiratory components, the initial impedance signals derived from several pairs of leads are preferably combined then filtered to extract the cardiac components. FIG. 4 illustrates actual data derived from a test subject having a partially fluidic lung. A first collection of graphs 121 illustrate impedance signals derived from the patient. The individual graphs illustrate individual signals each derived from a different pair of electrodes. Any of the signals can be selected for use in detecting the amplitudes of the cardiac and respiratory components. The single graph of the left illustrates a particular selected signal. As can be seen it includes both a respiratory component and a cardiac component. A second collection of graphs 123 illustrate the cardiac components only, which have been extracted by filtering the combined impedance signals of graphs 132. (Again, the graphs illustrate individual signals derived from different pairs of electrodes. The single graph of the left illustrates the selected signal.) A third collection of graphs 125 illustrate the cardiac components superimposed on the combined signals.

As noted above in the Summary, the reduction in peak-to-peak amplitude of an impedance-based respiration pattern is not due to diminished respiratory effort on the part of the patient but is instead due to the presence of the fluid in the lungs. In this regard, the fluids tend to reduce electrical impedance through the lungs. Hence, when impedance is detected, the presence of fluids within the lungs tends to diminish the impedance values. Hence, peak-to-peak variations in impedance due to respiratory activity are likewise diminished. The presence of fluids in the lungs, however, does not significantly change peak-to-peak variations in the cardiac component of the signal, thus allowing a comparison of the two components to be used the purposes of detecting pulmonary edema. In other words, the cardiac component essentially provides a baseline against which changes in the respiratory component can be reliably compared. Without the cardiac component, changes in impedance due to other factors might be misinterpreted as being indicative of the presence of fluids in the lungs.

Figure 5:
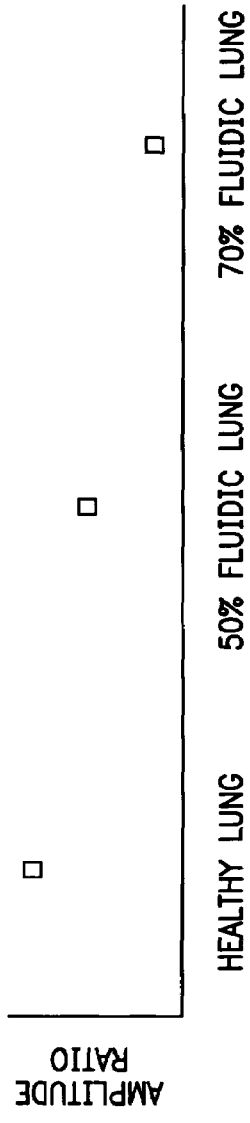
FIG. 5 is a graph of various amplitude ratio values employed by the method of FIG. 2 to detect pulmonary edema.
Figure 6:
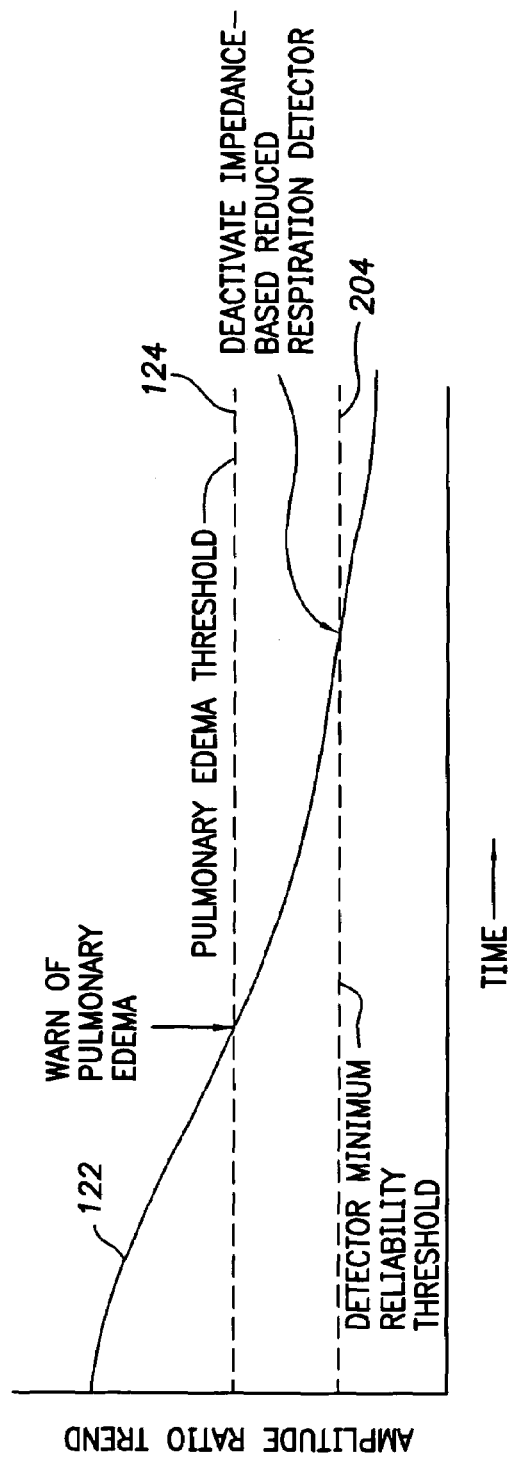
FIG. 6 is an exemplary, stylized graph of a trend pattern analyzed via the method of FIG. 2.

In one example, the ratio of the peak-to-peak amplitudes of the respiration pattern and the cardiac pattern are examined to detect pulmonary edema. This is illustrated in FIG. 5, which shows amplitude ratio of values (shown on arbitrary scale) for a healthy lung, a 50% fluidic lung, and a 70% fluidic lung. As can be seen, the amplitude ratio is highest for the healthy lung and is lowest for the 70% fluidic lung. Amplitude ratio values tracked over time allow for generation of a trend pattern for detecting the onset of pulmonary edema. This is illustrated in FIG. 6, by way of a stylized representation of a trend line 122. As can be seen, the amplitude ratio decreases over time. This is due to an increase in lung fluids as CHF progresses. A pulmonary edema detection threshold 124 is specified. Once the amplitude ratio falls below the edema detection threshold, pulmonary edema is thereby detected and appropriate warnings and therapy are delivered, as described in further detail below.

Hence, the amplitude ratio provides an effective and simple means for comparing impedance-based respiratory patterns and impedance-based cardiac patterns. However, other techniques for comparing the two patterns can instead be employed. In another example, for example, a power density spectrum is calculated based upon the impedance pattern. For a healthy lung, the power density spectrum exhibits two clearly identifiable peaks, one corresponding to the frequencies associated with respiration and the other corresponding to the frequencies associated with the beating of the heart. However, for a fluidic lung, the power density spectrum does not exhibit two clearly identifiable peaks. Rather, only a single peak representative of cardiac beating is clearly identifiable. Accordingly, a power density spectrum provides an alternative means for comparing the impedance-based respiratory patterns and the impedance-based cardiac patterns.

Still other comparison techniques may be employed and no attempt is made herein to list or identify all possible comparison techniques that may be used in connection with the invention. In the remaining descriptions, the use of the numerical ratio is primarily used, as this provides a simple and effective means for comparison.

Figure 7:
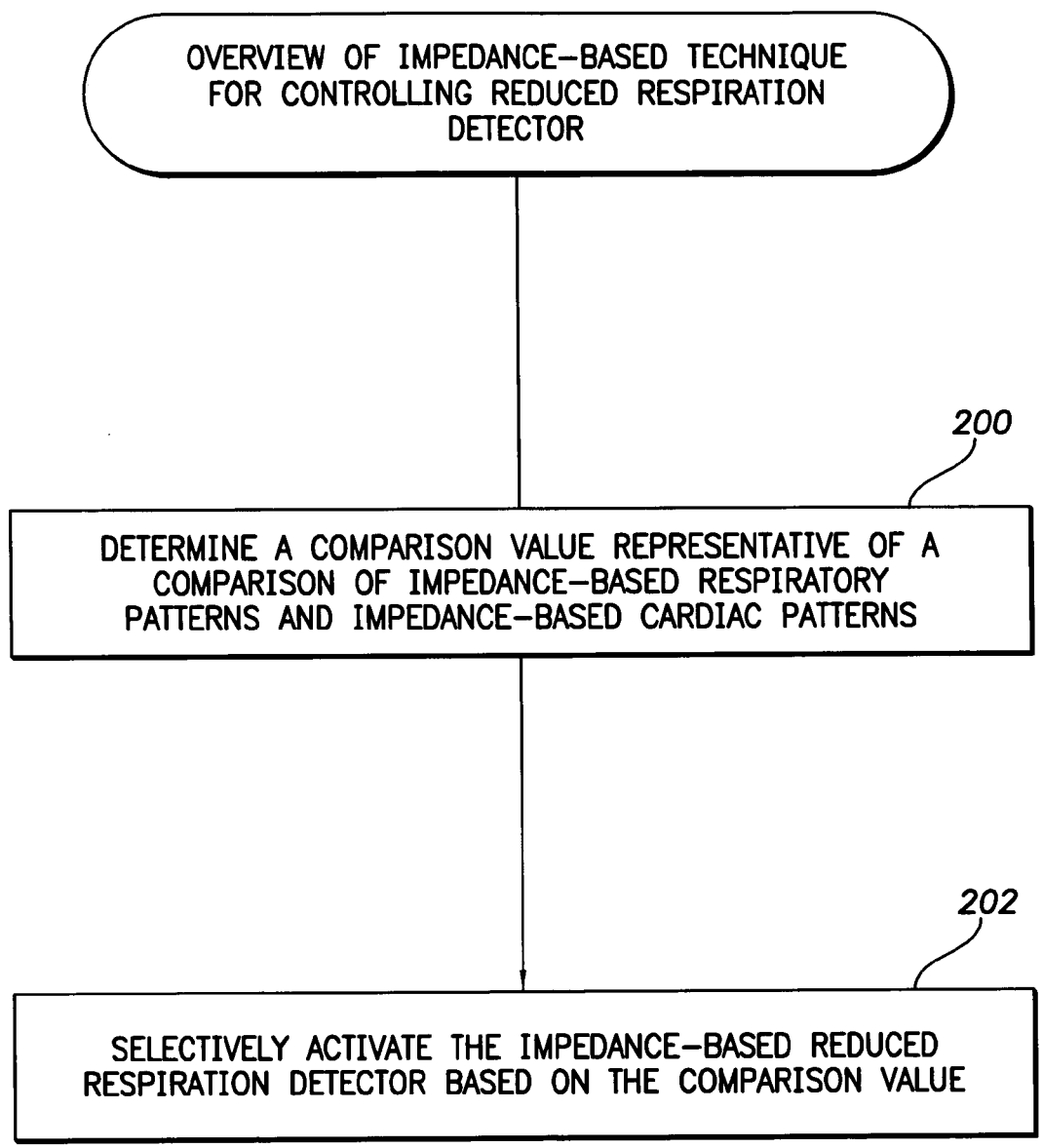
FIG. 7 is a flow diagram providing an overview of a method for controlling activation of the impedance-based reduced respiration detector of FIG. 1.

Overview of Comparison Technique for Determining Reliability of Reduced Respiration Detector FIG. 7 provides an overview of the techniques of the invention for use in determining the reliability of an impedance-based reduced respiration detector employed by an implantable medical device. Briefly, at step 200, the implantable medical device determines a comparison value representative of a comparison of impedance-based respiratory patterns and impedance-based cardiac patterns. Then, at step 202, the reduced respiration detector is selectively activated based on the comparison value. As explained in connection with FIG. 3, the presence of fluids within the lung reduces respiration amplitudes relative to cardiac amplitudes within the impedance signal. Once the respiration amplitude becomes too diminished, it becomes difficult or impossible to reliably detect respiration patterns from the impedance signals. For the example of a 70% fluidic lung, the respiration amplitude is not much greater than the cardiac amplitude, such that the "noise" within the signal due to cardiac beating makes it difficult to reliably extract respiration patterns. Even if low-pass filtering is used to illuminate the cardiac patterns and advanced signal processing techniques are applied to analyze the remaining signal components, it becomes increasingly difficult to reliably detect respiration patterns, at least for the purposes of detecting episodes of reduced respiration, such as apnea and hypopnea. Accordingly, any impedance-based reduced respiration detector employed by the implantable medical device is preferably deactivated if impedance-based respiratory patterns become too diminished relative to impedance-based cardiac patterns. In that case, alternative techniques for detecting reduced respiration are preferably initiated, such as external monitoring techniques, (e.g. nasal thermistors or chest band-based detectors), or implantable system-based techniques that do not rely on impedance signals, such as blood-pressure based techniques. See, for example, U.S. patent application Ser. No. 10/821,241, filed Apr. 7, 2004, entitled "System and Method for Apnea Detection Using Blood Pressure Detected via an Implantable Medical System" (A04P1034.).

Preferably, the ratio of the peak-to-peak amplitudes of the respiration pattern to the peak-to-peak amplitudes of the cardiac pattern is again calculated for use as the comparison value. Referring again to FIG. 6, the amplitude ratio continues to decrease until it falls below a reduced respiration detector minimum reliability threshold 204. Once the amplitude ratio falls below that threshold, the impedance-based reduced respiration detector is deactivated, appropriate warnings are generated and/or alternatives techniques are activated to detect episodes of reduced respiration. This is described in further detail below.

Exemplary Combined Technique

What have been described thus far are techniques either for detecting the pulmonary edema or for determining the reliability of an impedance-based reduced respiration detector. Preferably, the implantable medical device performs both types of analysis. This will be described by way of the example set forth in FIG. 8.

Preferably, the impedance-based analysis described herein is performed based on impedance signals sensed shortly after the patient falls asleep. The impedance signals are preferably sensed shortly after the patient falls asleep since it is thereby unlikely that a significant episode of apnea/hypopnea will already have occurred. If the analysis is performed on impedance signals sensed later during the sleep period of the patient, it is possible that an episode of reduced respiration will be ongoing at the time the signals are sensed, which could result in a false positive detection of pulmonary edema. The impedance signals are preferably sensed while the patient is asleep so that movement of the patient is limited, as such movement might adversely affect the reliability of impedance-based measurements. However, the techniques of the invention can potentially be exploited based on impedance signals sensed while the patient is awake, so long as appropriate steps are taken to identify periods of time while the patient is stationary for detecting the impedance signals or appropriate steps are taken to filter out any effects caused by patient motion.

Beginning at step 300, the pacer/ICD monitors patient activity to determine whether the patient is awake or sleep. Examples of sleep detection techniques are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device and Method for Varying Pacing Parameters to Mimic Circadian Cycles"; and U.S. patent application Ser. No. 10/339,989, to Koh et al., entitled "System and Method for Detecting Circadian States Using an Implantable Medical Device," filed Jan. 10, 2003.

The level of patient activity is compared against an activity threshold to determine whether the patient is asleep and, if so, step 302 is performed wherein impedance signals are sampled over a period of, for example, one minute. During steps 304 and 306, the impedance signals are low-pass filtered and high-pass filtered by digital signal processing method to yield respiratory patterns and cardiac patterns, respectively. Otherwise conventional hard-wired high-pass and low-pass filters may be employed. At steps 308 and 310, the filtered signals are analyzed to measure the peak-to-peak amplitudes in the patterns. Preferably, the peak-to-peak amplitude variations detected within the respiratory patterns over the one minute period are averaged (and, likewise, for the cardiac patterns.) At step 312, the numerical ratio between the averaged peak-to-peak amplitudes is calculated. At step 314, the ratio value is saved in device memory for tracking lung fluid trend, as shown, for example, in FIG. 6.

The latest amplitude ratio is then compared against the aforementioned pulmonary edema detection threshold and, if it is found to fall below the threshold, pulmonary edema is thereby detected, warning signals are issued, and appropriate therapy is initiated, at step 316. Specific procedures that may be performed during step 316 in response to pulmonary edema will be described in greater detail below, primarily with reference to FIG. 9. Otherwise routine techniques may be employed to the set an appropriate value for the pulmonary edema detection threshold. The threshold value may vary from patient to patient. In one example, a physician examines the trend in amplitude ratio values calculated at step 314 for the patient and then sets the pulmonary edema detection threshold for that patient based upon those values, in conjunction with the physician's knowledge of the condition of the patient. For example, if the patient is known to have normal, healthy lungs, the threshold may be set well below the ratio values detected for the patient. However, if the patient already has a fair amount of fluid in the lungs, the detection threshold may be set to a value closer to the current amplitude ratio values so that any further increase in lung fluids will be more promptly detected. Of course, if the patient is already known to have pulmonary edema, then the detection threshold need not be set, as no automatic detection of pulmonary edema is required in that case. Adaptive techniques may also be employed. In one example, a long term average and a short term average of amplitude ratio values are calculated and compared and any differences therebetween are tracked over time. A decrease in the short term average relative to the long term average is indicative of an increase in lung fluidity and vice versa.

The latest amplitude ratio value is also compared against the aforementioned minimum reliability threshold value to determine whether an impedance-based reduced respiration detector may reliably be employed.

So long as the amplitude ratio remains above the minimum reliability threshold, an impedance-based (i.e. Z-based) reduced respiration detector may still be reliably employed, step 318, to detect apnea or other episodes of reduced respiration. However, if the amplitude ratio falls below the minimum reliability threshold, then the impedance-based detector is likely to pick up cardiac components significantly, step 320, thus necessitating deactivation of the detector, at step 322. At that point, an alternative reduced respiration detector is preferably activated, such as a conventional external respiration detector. Also, at step 324, appropriate warnings are delivered of the patient or to his/her physician or other medical personnel. The minimum reliability threshold is preferably predetermined based on routine experimentation to specify a value below which respiration patterns cannot reliably be extracted from thoracic impedance signals. The particular value may depend upon the particular detector being used, as some detection techniques may be more effective than others at extracting respiration patterns from impedance signals even in the presence of pulmonary edema.

Although not shown, processing eventually returns to step 300 for further monitoring the patient activity to identify the next period of time when it is appropriate to detect and analyze impedance signals. Preferably, the impedance signals are detected and analyzed at least once per day, though more frequently in other implementations. Note that, in some implementations, rather than triggering warnings and therapy if a single value falls below one of the thresholds, no action is taken unless and until the ratio falls below the threshold for several consecutive days, so as to prevent anomalous data from triggering false positives. However, given that pulmonary edema can be fatal, it is typically better to deliver warnings promptly, even if there is the possibility of a false positive. Also note that, in the examples described thus far, the pulmonary edema threshold value is set higher than the reduced respiration minimum reliability threshold. However, in some implementations or for some patients or for use with some detectors, the thresholds may be reversed.

Response to Pulmonary Edema

Figure 8:
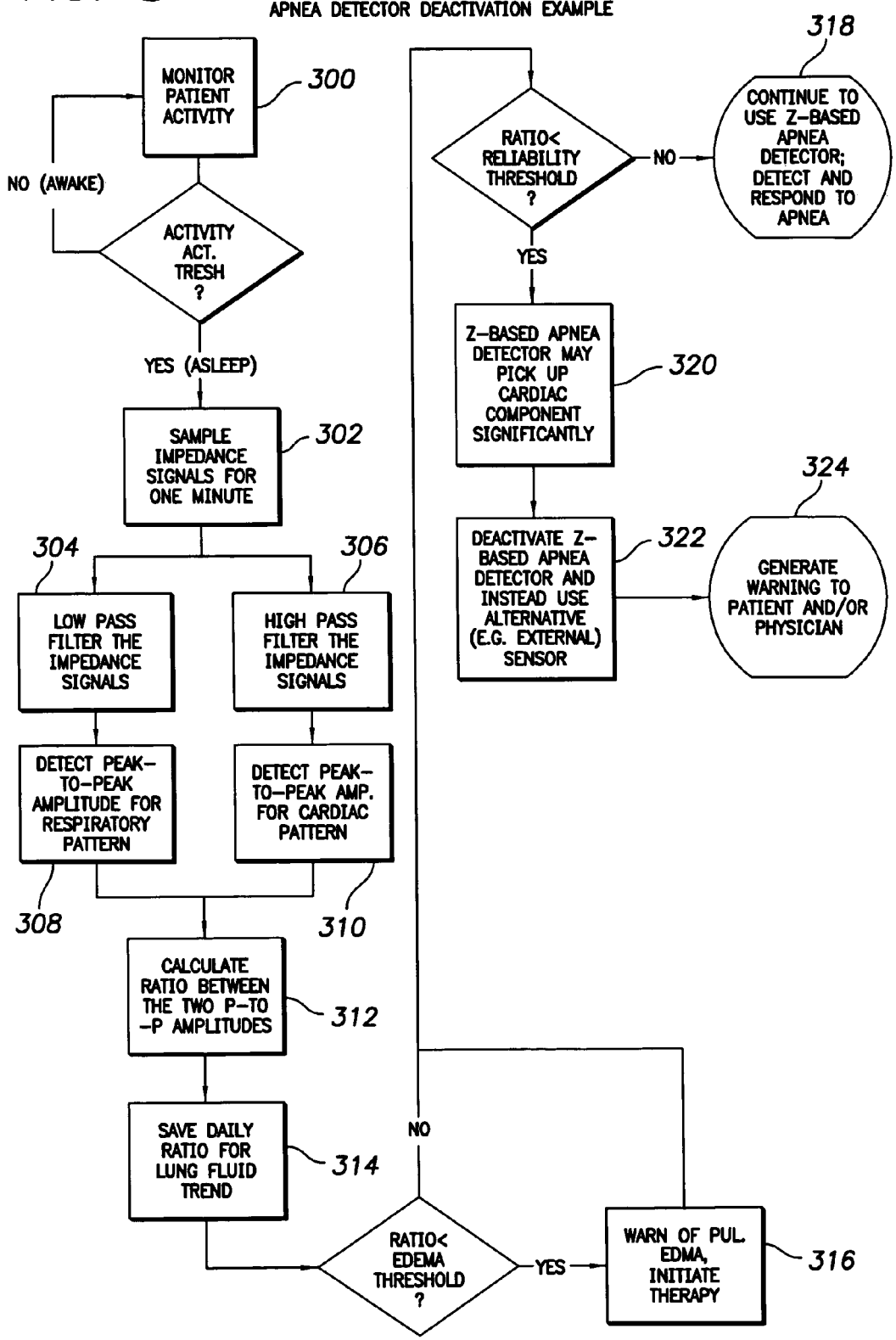
FIG. 8 is a flow diagram providing an example of a combined technique for detecting pulmonary edema and for controlling activation of an impedance-based reduced respiration detector for use with the system of FIG. 1.
Figure 9:
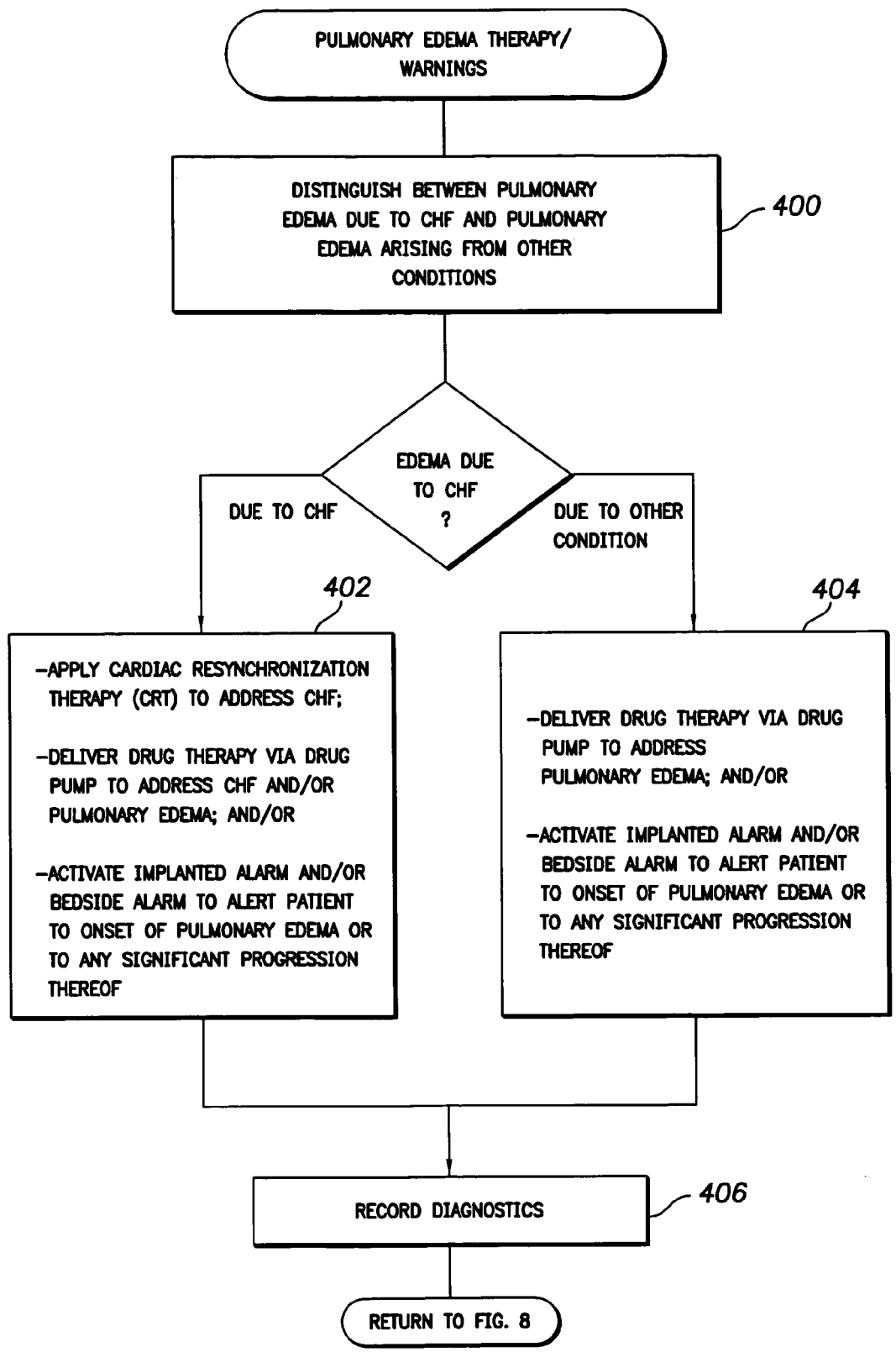
FIG. 9 is a flow chart summarizing responses implemented by the system of FIG. 1 in response to detection of pulmonary edema using the techniques of FIGS. 2-8.

Referring now to FIG. 9, therapy and warning signal generation activated at step 316 of FIG. 8 will be summarized. In the example of FIG. 9, therapy depends on whether the pulmonary edema is due to CHF or some other condition. Non-CHF-related pulmonary edema may be caused by, e.g., pneumonia, an excess of intravenous fluids, or some types of kidney disease, as well as bad burns, liver disease, nutritional problems, and/or Hodgkin's disease. Non-CHF-related pulmonary edema can also be caused by other conditions causing the lungs to not drain properly, or conditions where the respiratory veins are blocked.

If the pulmonary edema is due to CHF, then therapy is preferably delivered to address the underlying heart failure, as well as to address the pulmonary edema itself. At step 402, the pacer/ICD determines if the pulmonary edema is due to CHF. This may be accomplished by employing any of a variety of techniques for detecting CHF. Techniques for detecting or tracking heart failure including CHF are set forth the following patents and patent applications: U.S. patent application Ser. No. 11/100,008, of Kil et al., entitled "System And Method For Detecting Heart Failure And Pulmonary Edema Based On Ventricular End-Diastolic Pressure Using An Implantable Medical Device," filed Apr. 5, 2005; U.S. patent application Ser. No. 11/014,276, of Min et al., entitled "System And Method For Predicting Heart Failure Based On Ventricular End-Diastolic Volume/Pressure Using An Implantable Medical Device," filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004; U.S. patent application Ser. No. 10/346,809, of Min et al., entitled "System and Method for Monitoring Cardiac Function via Cardiac Sounds Using an Implantable Cardiac Stimulation Device," filed Jan. 17, 2003; and U.S. patent application Ser. No. 10/792,305, filed Mar. 2, 2004, entitled "System And Method For Diagnosing And Tracking Congestive Heart Failure Based On The Periodicity Of Cheyne-Stokes Respiration Using An Implantable Medical Device" (A04P1019). See also: U.S. Pat. No. 6,572,557, to Tchou et al., entitled "System and Method for Monitoring Progression of Cardiac Disease State Using Physiologic Sensors." U.S. Pat. No. 6,645,153, to Kroll et al., entitled "System and Method for Evaluating Risk of Mortality Due To Congestive Heart Failure Using Physiologic Sensors," and U.S. Pat. No. 6,438,408 to Mulligan et al., entitled "Implantable Medical Device For Monitoring Congestive Heart Failure."

If the pulmonary edema is due to CHF, then at step 402, CRT therapy is activated to address heart failure/pulmonary edema and/or drug therapy specific to heart failure/pulmonary edema is delivered to the patient. CRT and related therapies are discussed in the above-referenced patents to Mathis et al., Kramer et al., and Stahmann et al. The degree of severity of heart failure/pulmonary edema may be used to control CRT pacing parameters such as the time delay between left and right ventricular pulses to, for example, provide more aggressive CRT for more severe heart failure. Drug therapy is delivered using an implanted drug pump, if so equipped. Exemplary heart failure medications include ACE inhibitors, diuretics, digitalis and compounds such as captopril, enalapril, lisinopril and quinapril. Exemplary pulmonary edema medications include diuretics such as furosemide. Depending upon the particular medication, alternative compounds may be required for use in connection with an implantable drug pump. Routine experimentation may be employed to identify medications for treatment of heart failure and/or pulmonary edema that are safe and effective for use in connection with an implantable drug pump. Dosages may be titrated based upon the severity of heart failure/pulmonary edema. Implantable drug pumps for use in dispensing medications are discussed in U.S. Pat. No. 5,328,460 to Lord et al., entitled "Implantable Medication Infusion Pump Including Self-Contained Acoustic Fault Detection Apparatus."

Warning signals are generated using an implanted warning device, if so equipped, and/or using a bedside monitor. In particular, warnings are generated to alert the patient to the onset of pulmonary edema and to subsequently warn of any significant progression in pulmonary edema. The bedside monitor may be directly networked with a centralized computing system for forwarding any warning signals to the patient's physician. A system incorporating bedside monitoring units connected to a centralized external programmer system is described in U.S. Pat. No. 6,622,045 to Snell et al., "System and Method for Remote Programming of Implantable Cardiac Stimulation Devices." The aforementioned patent to Lord et al. discusses implantable "tickle" warning devices that may be used to deliver internal warning signals.

If pulmonary edema is not due to heart failure, then, at step 404, then heat failure related therapies and medications are not delivered. Rather, only those therapies and medications that are specific to pulmonary edema are delivered. For example, diuretics such as furosemide may be delivered via the implantable drug pump (assuming such medications are safe and effective for use with implantable drug pumps.) Alternatively, if the implantable device is equipped to determine the underlying condition, then therapy appropriate to that underlying condition may be delivered, if the system is so equipped.

Responses to Episodes of Reduced Respiration

Figure 10:
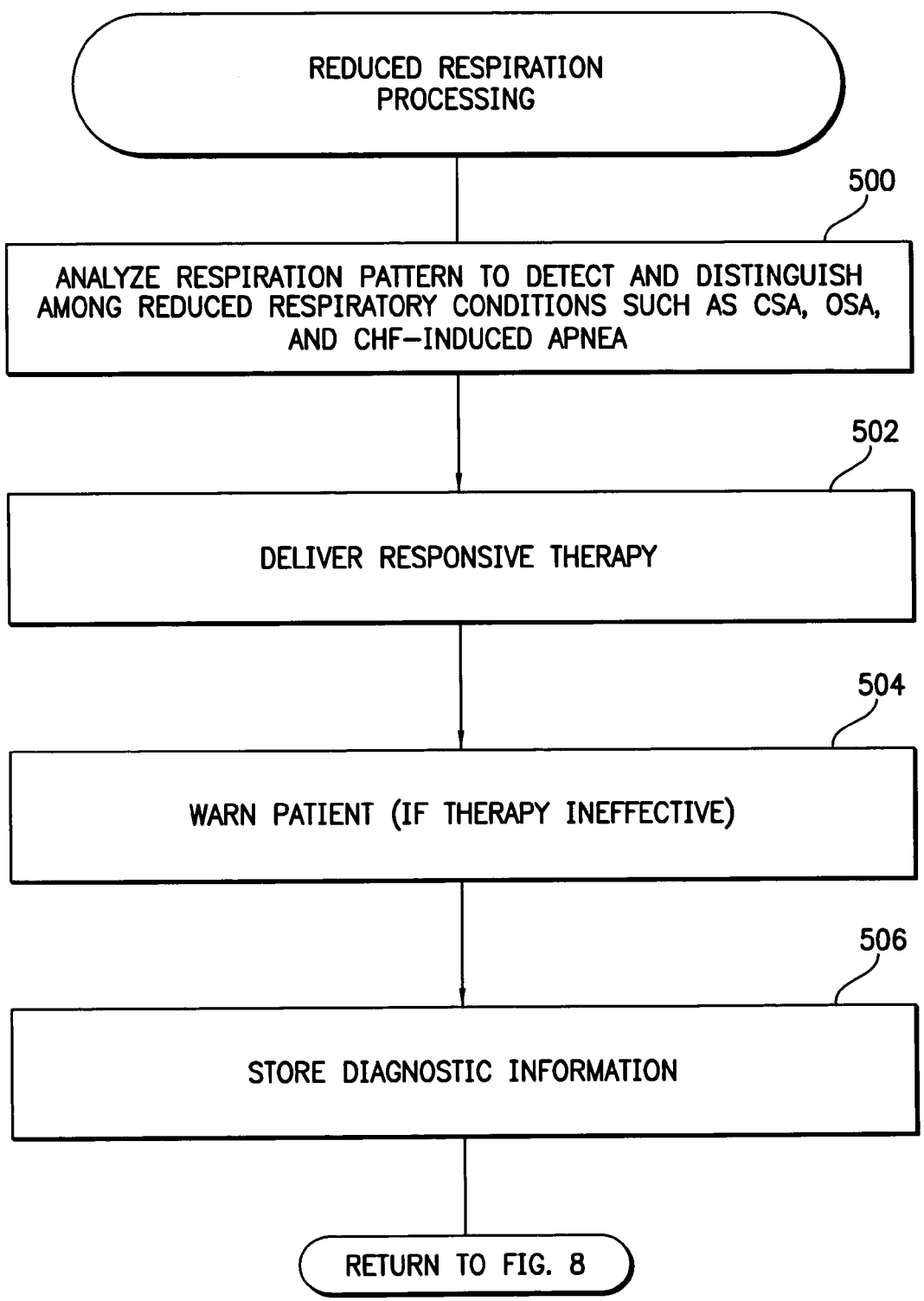
FIG. 10 is a flow chart summarizing responses implemented by the system of FIG. 1 in response to detection of episodes of reduced respiration.

Referring to FIG. 10, therapy and warning signal generation activated at step 318 of FIG. 8 will be summarized. If an episode of reduced respiration has been detected then, at step 500, the pacer/ICD analyzes the respiration pattern to detect and distinguish among reduced respiratory conditions such as CSA, OSA, and CHF-induced apnea. Techniques for detecting and distinguishing such conditions are set forth in U.S. patent application Ser. No. 10/795,009, of Koh, entitled "System and Method for Distinguishing among Obstructive Sleep Apnea, Central Sleep Apnea and Normal Sleep Using an Implantable Medical System," filed Mar. 4, 2004. At step 502, the pacer/ICD delivers appropriate therapy (assuming it is properly equipped). Therapy may depend upon whether episodes of reduced respiration occur frequently within the patient. For example, in response to detection of frequent episodes of CSA or CHF-induced apnea, atrial overdrive pacing therapy may be applied in an attempt to prevent the onset of additional episodes. A particularly effective atrial overdrive pacing technique, referred to herein as dynamic atrial overdrive (DAO) pacing, is described in U.S. Pat. No. 6,519,493 to Florio et al., entitled "Methods and Apparatus for Overdrive Pacing Heart Tissue Using an Implantable Cardiac Stimulation Device." Routine experimentation may be performed to identify optimal DAO pacing parameters for use with patients with apnea/hypopnea. The aggressiveness of DAO therapy may be adjusted based upon the frequency or duration of episodes of apnea/hypopnea.

Anti-apneic medications may be delivered via an implantable drug pump, if so equipped. Examples of medications that may be helpful in patients with apnea are set forth the following patents: U.S. Pat. No. 6,331,536 to Radulovacki et al., entitled "Pharmacological Treatment for Sleep Apnea"; U.S. Pat. No. 6,432,956 to Dement et al., entitled "Method for Treatment of Sleep Apneas"; U.S. Pat. No. 6,586,478 to Ackman et al., entitled "Methods and Compositions for Improving Sleep"; and U.S. Pat. No. 6,525,073 to Mendel et al., entitled "Prevention or Treatment of Insomnia with a Neurokinin-1 Receptor Antagonist." Depending upon the particular medication, alternative compounds may be required for use in connection with an implantable drug pump. Routine experimentation may be employed to identify medications for treatment of sleep apnea that are safe and effective for use in connection with an implantable drug pump. Dosages may be titrated based upon the frequency or duration of episodes of apnea.

If implantable phrenic nerve stimulators are implanted, CSA or CHF-induced apnea therapy can also involve delivery of rhythmic electrical stimulation to the phrenic nerves to mimic breathing (assuming the apnea/hypopnea is due to a lack of phrenic nerve signals.) Examples of phrenic nerve stimulators are set forth in U.S. Pat. No. 5,056,519 to Vince, entitled "Unilateral Diaphragmatic Pacer" and in U.S. Pat. No. 6,415,183 to Scheiner et al., entitled "Method and Apparatus for Diaphragmatic Pacing," which are incorporated by reference herein. Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles.

If upper airway stimulators are implanted, then OSA therapy can involve stimulating adjacent muscles to increase muscle tone and expand the airway, thus alleviating airway blockage associated with OSA. Upper airway stimulators are discussed in the patent application to Koh cited above and entitled "System and Method for Distinguishing among Obstructive Sleep Apnea, Central Sleep Apnea and Normal Sleep Using an Implantable Medical System." If an implantable hypoglossyl nerve stimulator is implanted, therapy can also involve delivery of stimulation to the hypoglossyl nerves in response to OSA. Examples of hypoglossyl nerve stimulators are set forth in U.S. Patent Application 2003/0216789 of Deem et al., entitled "Method and System for Treating Sleep Apnea."

For therapy for use for apnea occurring during CSR, see U.S. patent application Ser. No. 10/829,719, filed Apr. 21, 2004, entitled "System and Method for Applying Therapy during Hyperpnea Phase of Periodic Breathing Using an Implantable Medical Device" (A04P1037).

Additional techniques may be used, if desired, to corroborate the detection of an episode of reduced respiration made using the techniques of the invention before therapy is delivered. See, e.g., U.S. patent application Ser. No. 10/883,857, filed Jun. 30, 2004, entitled "System And Method For Real-Time Apnea/Hypopnea Detection Using An Implantable Medical System (A04P1057) and U.S. patent application Ser. No. 10/821,241, filed Apr. 7, 2004, entitled "System And Method For Apnea Detection Using Blood Pressure Detected via an Implantable Medical System" (A04P1034).

Continuing with FIG. 10, at step 504, suitable warning signals may be delivered to alert the patient, his/her physician or other medical personnel to any episodes of reduced breathing. During an actual episode of reduced respiration, the implantable alarm (alarm 20 of FIG. 1) may be activated to awaken the patient (assuming the patient is sleeping) in an attempt to terminate the episode of apnea/hypopnea. Alternatively, the bedside alarm may be activated by transmission of appropriate wireless control signals. Activation of an alarm to awaken the patient is preferably employed only if therapy is found to be ineffective, since awakening the patient interrupts with the patient's natural sleeping patterns. In any case, whenever some form of apnea/hypopnea therapy is delivered, appropriate diagnostic information is stored (at step 506) so that if medical professional can subsequently review the therapy and evaluate its effectiveness.

What have been described are various techniques for detecting pulmonary edema and/or detecting episodes of reduced respiration and delivering appropriate therapy. For the sake of completeness, a detailed description of an exemplary pacer/ICD for controlling these functions will now be provided. However, principles of invention may be implemented within other pacer/ICD implementations or within other implantable devices.

Pacemaker/ICD

FIG. 11 provides a simplified block diagram of the pacer/ICD, which is a multi-chamber stimulation device capable of treating both fast and slow arrhythmias with stimulation therapy, including cardioversion, defibrillation, and pacing stimulation (as well as capable of tracking respiration, detecting episodes of abnormal respiration and delivering appropriate therapy.) To provide atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 11, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 12:
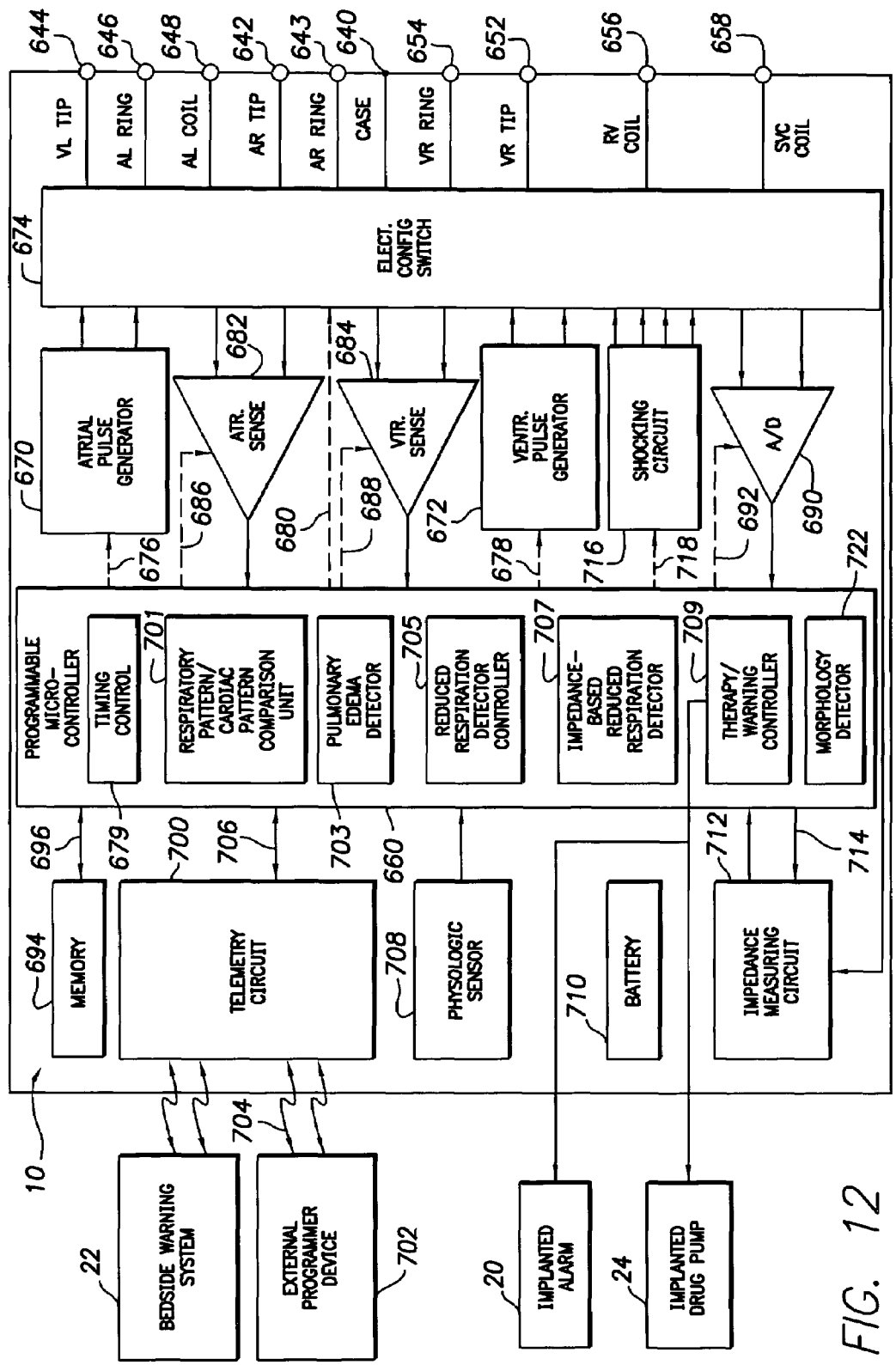
FIG. 12 is a functional block diagram of the pacer/ICD of FIG. 11, illustrating basic circuit elements that provide cardioversion, defibrillation and/or pacing stimulation in four chambers of the heart and particularly illustrating impedance-based components for detecting pulmonary edema and for controlling an impedance-based reduced respiration detector.

A simplified block diagram of internal components of pacer/ICD 10 is shown in FIG. 12. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 640 for pacer/ICD 10, shown schematically in FIG. 12, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 643. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively. Separate terminals (not shown) may be provided for connecting the implanted warning/reminder device 18 and the implanted drug pump 20, which are instead shown coupled directly to internal functional components of the pacer/ICD that control these devices.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 12, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 10, it is to be understood that the sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 12. The battery 710 may vary depending on the capabilities of pacer/ICD 10. If the system only provides low voltage therapy, a lithium iodine or lithium copper fluoride cell may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 12, pacer/ICD 10 is shown as having an impedance measuring circuit 712 which is enabled by the microcontroller 660 via a control signal 714. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 60 also includes a respiratory pattern/cardiac pattern comparison unit 701 operative to determine a comparison value representative of a comparison of impedance-based respiratory patterns and impedance-based cardiac patterns. A pulmonary edema detector 703 is operative to detect pulmonary edema based on the comparison value. A reduced respiration detector controller 705 is operative to selectively activate an impedance-based reduced respiration detector 707 based on the comparison value. Additionally, a therapy controller 709 is provided for controlling therapy in response to pulmonary edema and/or in response to episodes of reduced respiration. Depending upon the implementation, the various components may be implemented as separate software modules. However, the modules may be combined so as to permit single modules to perform multiple functions. Note also that, although these components are shown as being sub-components of the microcontroller, the components may be instead implemented separately from the microcontroller.

The principles of the invention may be exploiting using other implantable systems or in accordance with other techniques. Thus, while the invention has been described with reference to particular exemplary embodiments, modifications can be made thereto without departing from scope of the invention. The various functional components of the exemplary systems described herein may be implemented using any appropriate technology including, for example, microprocessors running software programs or application specific integrated circuits (ASICs) executing hard-wired logic operations. Note also that the term "including" as used herein is intended to be inclusive, i.e. "including but not limited to."

What is claimed is:

1. A system for use with an implantable medical device for implant within a patient, the system comprising:
   a respiratory pattern/cardiac pattern comparison unit operative to determine a comparison value representative of a comparison of impedance-based respiratory patterns and impedance-based cardiac patterns, wherein the respiratory pattern/cardiac pattern comparison unit determines the comparison value by comparing amplitudes of the respiratory and cardiac patterns; and
   a pulmonary edema detector operative to detect pulmonary edema based on the comparison value.

2. The system of claim 1 further comprising:
   an impedance-based reduced respiration detector operative to detect an episode of reduced respiration; and
   a controller operative to selectively activate the impedance-based reduced respiration detector based on the comparison value.

3. A system for use with an implantable medical device for implant within a patient, the system comprising:
   means for detecting impedance;
   means for detecting cardiac patterns based on thoracic impedance;
   means for detecting respiratory patterns based on thoracic impedance;
   means for comparing amplitudes of the respiratory patterns and cardiac patterns; and
   means for detecting pulmonary edema based on the comparison.

4. The system of claim 3 and further comprising means for delivering therapy in response to detecting pulmonary edema.

5. The system of claim 3 and further comprising means for generating a warning in response to detecting pulmonary edema.

* * * * *